(12) United States Patent
Lieb et al.

(10) Patent No.: US 6,441,030 B1
(45) Date of Patent: Aug. 27, 2002

(54) 3-PHENYL-PYRONES

(75) Inventors: Folker Lieb, Leverkusen; Reiner Fischer, Monheim; Alan Graff; Udo Schneider, both of Leverkusen; Michael Ruther, Langenfeld; Christoph Erdelen, Leichlingen; Wolfram Andersch, Bergisch Gladbach; Ulrike Wachendorff-Neumann, Neuwied; Gerd Hänssler, Leverkusen; Astrid Mauler-Machnik, Leichlingen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/807,135

(22) PCT Filed: Sep. 24, 1999

(86) PCT No.: PCT/EP99/07113

§ 371 (c)(1),
(2), (4) Date: Apr. 6, 2001

(87) PCT Pub. No.: WO00/21946

PCT Pub. Date: Apr. 20, 2000

(30) Foreign Application Priority Data

Oct. 9, 1998 (DE) .......................... 198 46 517

(51) Int. Cl.⁷ .......................... A01N 43/16; A61K 31/35
(52) U.S. Cl. ................... 514/460; 514/336; 514/444; 549/60; 549/292; 546/282.1; 504/292
(58) Field of Search ............... 549/60, 292; 546/282.1; 504/292; 514/336, 444, 460

(56) References Cited

U.S. PATENT DOCUMENTS 3,542,809 A 11/1970 Nakanishi ................ 260/332.2
6,071,937 A  6/2000 Bretschneider et al. ..... 514/336

FOREIGN PATENT DOCUMENTS

EP  0 588 137  3/1994
WO  94/29268  12/1994

OTHER PUBLICATIONS

Organic Preparations and Procedures Int. 7(4), pp. 155–158, 1975, Susumu Nakanishi and Kenneth Butler, Synthesis of Chlorocarbonyl Ketenes.

*Primary Examiner*—Amelia Owens
(74) *Attorney, Agent, or Firm*—Joseph C. Gil; John E. Mrozinski, Jr.

(57) ABSTRACT

Novel 3-phenyl-pyrones of the formula

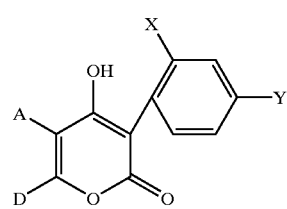

in which

A, D, X and Y are each as defined in the description, a process for preparing these substances and their use as pesticides, fungicides and herbicides.

10 Claims, No Drawings

3-PHENYL-PYRONES

FIELD OF THE INVENTION

The present invention relates to novel 3-phenyl-pyrones, to a process for their preparation and to their use as pesticides, fungicides and herbicides.

BACKGROUND OF THE INVENTION

Numerous oxymethoxy-3-phenyl-pyrone derivatives having pesticidal, fungicidal and herbicidal properties have already been disclosed (c.f. WO 97-19 941). The activity of these substances is good; however, at low application rates and at certain indications, it sometimes leaves something to be desired.

Furthermore 3-(2-methyl-4-fluorophenyl)-4-hydroxy-5-methyl-6-(pyrid-2-yl)-pyrone and 3-(2-methyl4-chlorophenyl)-4-hydroxy-5-methyl-6-(4-fluorophenyl)-pyrone have already been described as intermediates (cf. WO 97-19 941). However, biological properties of these substances have hitherto not been mentioned.

SUMMARY OF THE INVENTION

Novel 3-phenyl-pyrones of the formula

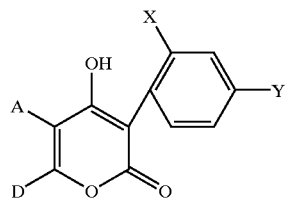

have pesticidal, and herbicidal activity.

DETAILED DESCRIPTION

This invention, accordingly, provides novel 3-phenyl-pyrones of the formula

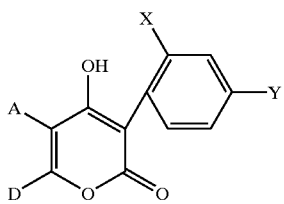

(I)

in which
X represents alkyl and
Y represents halogen
X represents halogen and
Y represents alkyl,
A represents hydrogen, alkyl or optionally substituted aryl and
D represents hydrogen, alkyl, optionally substituted cycloalkyl, optionally substituted aryl or optionally substituted heterocyclyl, or
D represents a radical of the formula

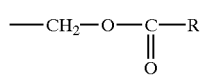

in which
R represents optionally substituted phenyl, or

A and D together with the carbon atoms to which they are attached represent an optionally substituted carbocycle or represent an optionally substituted heterocycle, except for the compounds of the formulae

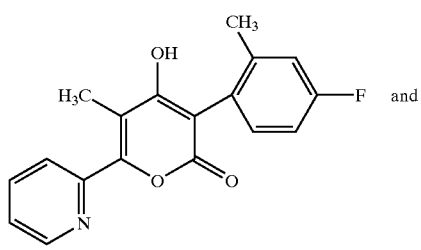

and

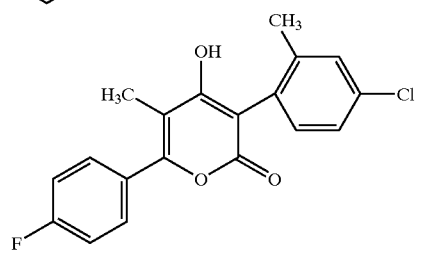

Depending on the nature of the substituents, the compounds of the formula (I) can be present as geometrical and/or optical isomers or isomer mixtures of varying composition, which can, if desired, be separated in a customary manner. The present invention relates both to the pure isomers and to isomer mixtures. For the sake of simplicity, hereinbelow 3-phenyl-pyrones of the formula (I) are always referred to, although this may mean both the pure isomers and, if appropriate, also mixtures having various proportions of isomers.

The 3-phenyl-pyrones of the formula (I) can be depicted by the formula

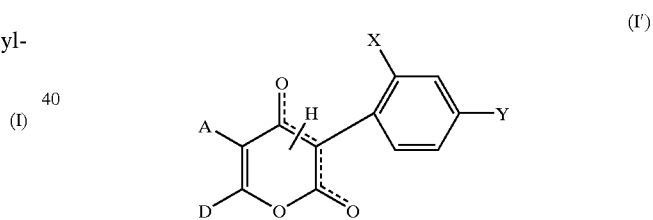

(I')

The broken line is meant to indicate that these substances can be present in the two tautomeric forms

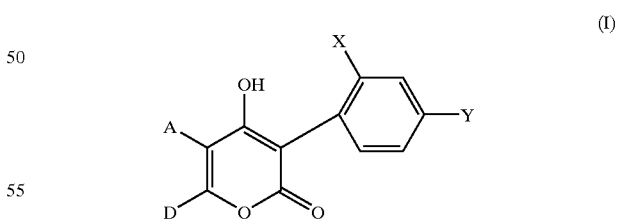

(I)

and

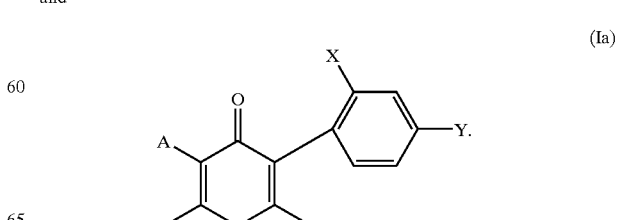

(Ia)

The 3-phenyl-pyrones according to the invention can be present as mixtures of compounds of the formulae (I) and (Ia), or else in the form of pure isomers. Mixtures of compounds of the formulae (1) and (Ia) can be separated by physical means, for example by chromatographic methods.

For reasons of clarity, hereinbelow only one of the possible isomers is shown in each case. This does not exclude that the compounds, if appropriate, may be present in the form of the isomer mixtures or in the other isomeric form in question.

Furthermore, it has been found that the 3-phenyl-pyrones of the formula (I) can be prepared by reacting α) either carbonyl compounds of the formula

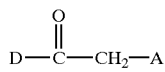

(II)

in which
A and D are each as defined above or

β) silyl ethers of the formula

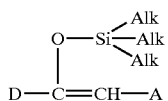

(III)

in which
A and D are each as defined above and
Alk represents alkyl having 1 to 4 carbon atoms,
in each case with ketene derivatives of the formula

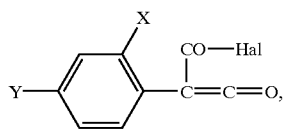

(IV)

in which
X and Y are each as defined above and
Hal represents chlorine or bromine,
if appropriate in the presence of a diluent and if appropriate in the presence of an acid acceptor.

Finally, it has been found that the 3-phenyl-pyrones of the formula (I) according to the invention have very good pesticidal, fungicidal and herbicidal activity.

Surprisingly, the 3-phenyl-pyrones of the formula (I) according to the invention are more suitable for use as pesticides, fungicides and herbicides than the constitutionally most similar prior-art active compounds of the same direction of action.

The formula (I) provides a general definition of the 3-phenyl-pyrones according to the invention. Preference is given to compounds of the formula (I), in which
X represents alkyl having 1 to 6 carbon atoms and
Y represents fluorine, chlorine or bromine or
X represents fluorine, chlorine or bromine and
Y represents alkyl having 1 to 6 carbon atoms.
A preferably represents hydrogen, alkyl having 1 to 12 carbon atoms or represents phenyl which may be mono- to trisubstituted by identical or different substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano and nitro, D preferably represents hydrogen, alkyl having 1 to 12 carbon atoms, represents cycloalkyl having 3 to 8 carbon atoms which is optionally substituted by halogen, alkyl having 1 to 4 carbon atoms, alkoxy having 1 to 4 carbon atoms and/or halogenoalkyl having 1 to 4 carbon atoms,
or represents phenyl which may be mono- to trisubstituted by identical or different substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano, nitro, phenyl and/or phenoxy, where the two lastmentioned radicals for their part may be mono- or disubstituted by halogen, $C_1$–$C_4$-alkyl, $C_1$–$C_4$-alkoxy, $C_1$–$C_4$-halogenoalkyl and/or $C_1$–$C_4$-halogenoalkoxy,
or represents 5- or 6-membered heteroaryl having 1 or 2 heteroatoms selected from the group consisting of oxygen, sulphur and nitrogen, where these radicals may be mono- or disubstituted by halogen, $C_1$–$C_6$-alkyl, $C_1$–$C_6$-halogenoalkyl, $C_1$–$C_6$-alkoxy, $C_1$–$C_6$-halogenoalkoxy, cyano and/or nitro,
or represents a radical of the formula

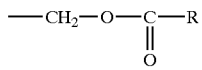

in which
R preferably represents phenyl which may be mono- to trisubstituted by identical or different substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano and/or nitro,
A and D together furthermore also preferably represent a $C_3$-$C_6$-alkanediyl, $C_3$–$C_6$-alkenediyl or $C_4$-$C_6$-alkanedienediyl group in which in each case optionally one methylene group is replaced by oxygen or sulphur, and which are in each case optionally substituted by halogen, $C_1$–$C_6$-alkyl, $C_1$–$C_6$-halogenoalkyl, $C_1$–$C_6$-alkoxy, $C_1$–$C_6$-halogenoalkoxy, or by a further $C_3$–$C_6$-alkanediyl-, $C_3$–$C_6$-alkenediyl- or $C_4$-$C_6$-alkanedienediyl group which forms a fused-on ring and in which in each case optionally one methylene group is replaced by oxygen or sulphur and which are optionally substituted by $C_1$–$C_6$-alkyl.

In the compounds of the formula (I), particularly preferably,
X represents alkyl having 1 to 4 carbon atoms and
Y represents fluorine, chlorine or bromine or
X represents chlorine or bromine and
Y represents alkyl having 1 to 4 carbon atoms,
A particularly preferably represents hydrogen, alkyl having 1 to 8 carbon atoms or represents phenyl which may be mono- to trisubstituted by identical or different substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and nitro,
D particularly preferably represents hydrogen, alkyl having 1 to 10 carbon atoms, represents cycloalkyl having 3 to 7 carbon atoms which is optionally mono- to trisubstituted by identical or different substituents selected from the group consisting of fluorine, chlorine, $C_1$–$C_3$-alkyl, $C_1$–$C_2$-alkoxy, $C_1$–$C_2$-halogenoalkyl,
or represents phenyl which may be mono- to trisubstituted by identical or different substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano, nitro, phenyl and/or phenoxy, where the two last mentioned radicals for their part may be mono- or disubstituted by fluorine, chlorine, bromine, methyl, ethyl, methoxy, trifluoromethyl, trifluoromethoxy and/or difluoromethoxy, or represents furanyl, pyridyl, imidazolyl, triazolyl, pyrazolyl, pyrimidinyl, thiazolyl or thienyl, where these radicals may be mono- or disubstituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and/or nitro, or D particularly preferably represents a radical of the formula

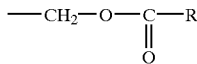

in which

R particularly preferably represents phenyl which may be mono- to trisubstituted by identical or different substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and/or nitro, A and D together furthermore particularly preferably represent a $C_3$–$C_5$-alkanediyl or $C_3$–$C_5$-alkenediyl group in which in each case optionally one carbon atom is replaced by oxygen or sulphur and which are optionally substituted by fluorine, chlorine, bromine, $C_1$–$C_4$-alkyl, $C_1$–$C_4$-alkoxy, $C_1$–$C_4$-halogenoalkyl and/or $C_1$–$C_6$-halogenoalkoxy, or by a further $C_4$-alkanedienediyl group which forms a fused-on ring and which may be substituted by $C_1$–$C_4$-alkyl.

In the compounds of the formula (I), very particularly preferably,

X represents methyl or ethyl and

Y represents fluorine or chlorine or

X represents chlorine or bromine and

Y represents methyl or ethyl,

A very particularly preferably represents hydrogen, alkyl having 1 to 6 carbon atoms or represents phenyl which may be mono- or disubstituted by identical or different substituents selected from the group consisting -of fluorine, chlorine, methyl, ethyl, n-propyl, isopropyl, trifluoromethyl, methoxy, ethoxy, trifluoromethoxy, cyano and nitro, D very particularly preferably represents hydrogen, alkyl having 1 to 8 carbon atoms, or represents cycloalkyl having 3 to 7 carbon atoms which is optionally mono- or disubstituted by identical or different substituents selected from the group consisting of fluorine, chlorine, methyl, ethyl, methoxy, ethoxy and trifluoromethyl, or represents phenyl which may be mono- or disubstituted by identical or different substituents selected from the group consisting of fluorine, chlorine, bromine, methyl, ethyl, n-propyl, isopropyl, n-butyl, sec-butyl, iso-butyl, tert-butyl, trifluoromethyl, methoxy, ethoxy, trifluoromethoxy, cyano, nitro, phenyl and phenoxy, where the two lastmentioned radicals for their part may be mono- or disubstituted by fluorine, chlorine, methyl, methoxy, trifluoromethyl and/or trifluoromethoxy, or represents furanyl, pyridyl or thienyl, where these radicals may be mono- or disubstituted by fluorine, chlorine, bromine, methyl, ethyl, n-propyl, isopropyl, trifluoromethyl, trifluoromethoxy, cyano and/or nitro, or D very particularly preferably represents a radical of the formula

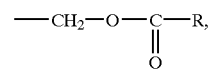

in which

R particularly preferably represents phenyl which may be mono- or disubstituted by identical or different substituents selected from the group consisting of fluorine, chlorine, methyl, ethyl, trifluoromethyl, methoxy, trifluoromethoxy, cyano and nitro, A and D together furthermore very particularly preferably represent a $C_3$–$C_5$-alkanediyl or $C_3$–$C_5$-alkenediyl group in which in each case optionally one methylene group is replaced by oxygen or sulphur and which is optionally mono- to tetrasubstituted by identical or different substituents selected from the group consisting of fluorine, chlorine, bromine, methyl, ethyl, n-propyl, isopropyl, n-butyl, iso-butyl, sec-butyl, tert-butyl, methoxy, trifluoromethyl and trifluoromethoxy, or by a further butadienediyl group which forms a fused-on ring and which may be mono- or disubstituted by methyl.

The abovementioned general or preferred radical definitions or illustrations can be combined with each other at will, i.e. including combinations between the ranges and preferred ranges in question. They apply both to the end products and, correspondingly, to the precursors and intermediates. Additionally, individual definitions may not be applicable.

Excluded from the 3-phenyl-pyrones according to the invention are, as already mentioned above, in each case the compounds of the formulae

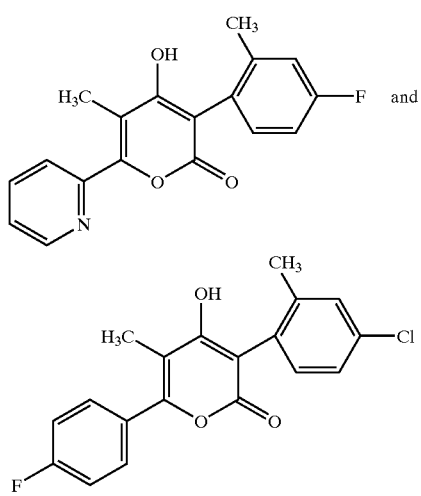

In addition to the 3-phenyl-pyrones mentioned in the Preparation Examples, the following substances of the formula (I) may be mentioned specifically:

TABLE 1
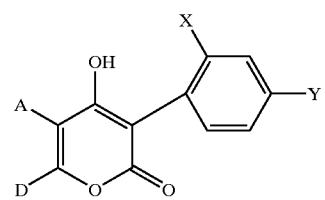
X = Br; Y = CH₃
| A | D |
|---|---|
| H | —C(CH₃)₃ |
| CH₃ | —CH₃ |
| CH₃ | —CH₂CHCH₃CH₂CH₃ |
| CH₃ | 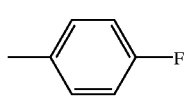 |
| CH₃ |  |
| CH₃ | 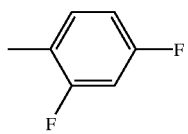 |
| CH₃ | 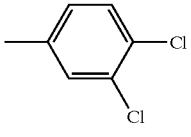 |
| CH₃ | 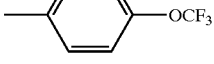 |
| 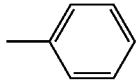 | CH₃ |
| CH₃ | 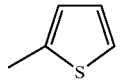 |
| CH₃ | 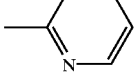 |
| CH₃ | 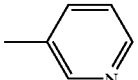 |
| CH₃ | 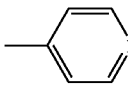 |
| CH₃ | 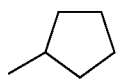 |
TABLE 1-continued
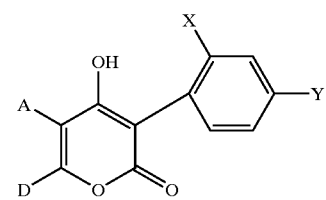
X = Br; Y = CH₃
| A | D |
|---|---|
| CH₃ |  |
| H |  |
|  | —(CH₂)₃— |
|  | —(CH₂)₄— |
|  | —C(CH₃)₂OC(CH₃)₂— |
|  | —CH=C(CH₃)—CH=C(CH₃)— |
|  | —C(CH₃)=CH—C(CH₃)=CH— |
|  | —CH=CBr—CH=CH— |
|  | —CH=CH—CH=C(OCH₃)— |
|  | —CH=CH—CCl=CH— |
|  | —C(CH₃)=CH—CH=C(CH₃)— |
|  | —CH=C(CF₃)—CH=CH— |
|  | —CH=CH—C(CF₃)=CH— |
|  | —CH=CH—CH=CH— |
TABLE 2
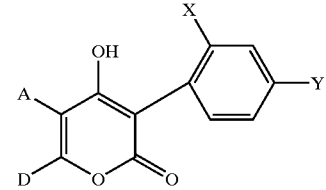
X = CH₃; Y = Cl
| A | D |
|---|---|
| H | —C(CH₃)₃ |
| CH₃ | —CH₂CHCH₃CH₂CH₃ |

TABLE 2-continued
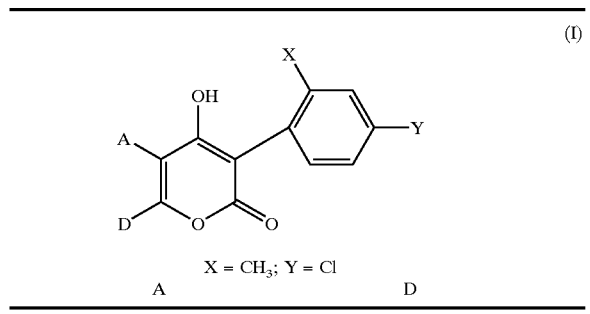
X = CH₃; Y = Cl
| A | D |
|---|---|
| CH₃ | 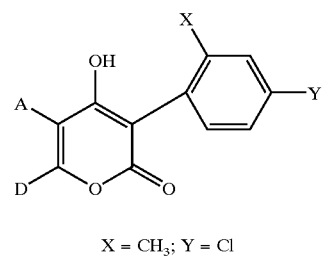 |
| CH₃ | 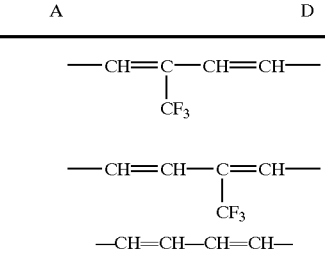 |
| CH₃ | 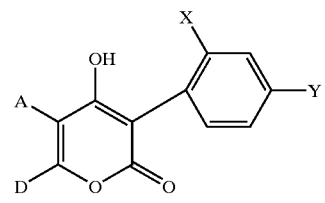 |
| CH₃ | 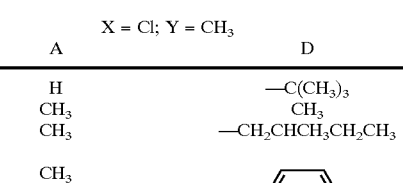 |
| CH₃ | 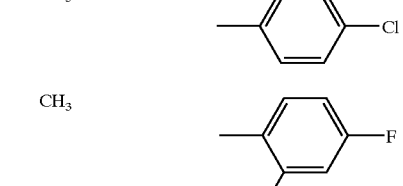 |
| CH₃ | 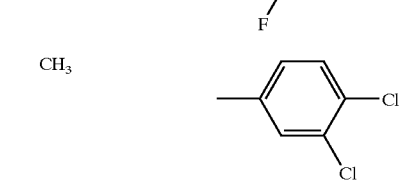 |
| H | 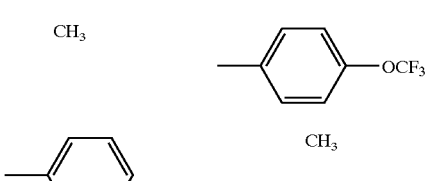 |
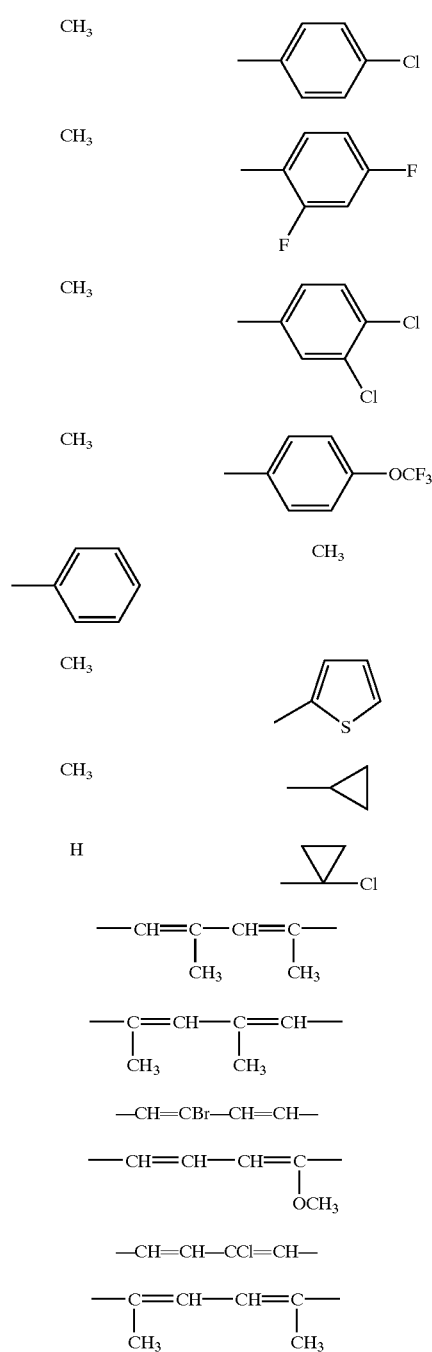
TABLE 2-continued
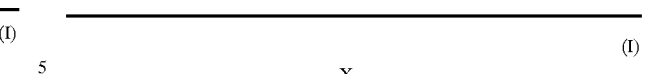
X = CH₃; Y = Cl
| A | D |
|---|---|
| | —CH=C—CH=CH—<br>     \|<br>    CF₃ |
| | —CH=CH—C=CH—<br>          \|<br>         CF₃ |
| | —CH=CH—CH=CH— |
TABLE 3
X = Cl; Y = CH₃
| A | D |
|---|---|
| H | —C(CH₃)₃ |
| CH₃ | CH₃ |
| CH₃ | —CH₂CHCH₃CH₂CH₃ |
| CH₃ |  |
| CH₃ |  |
| CH₃ | |
| CH₃ | |
| | |

TABLE 3-continued

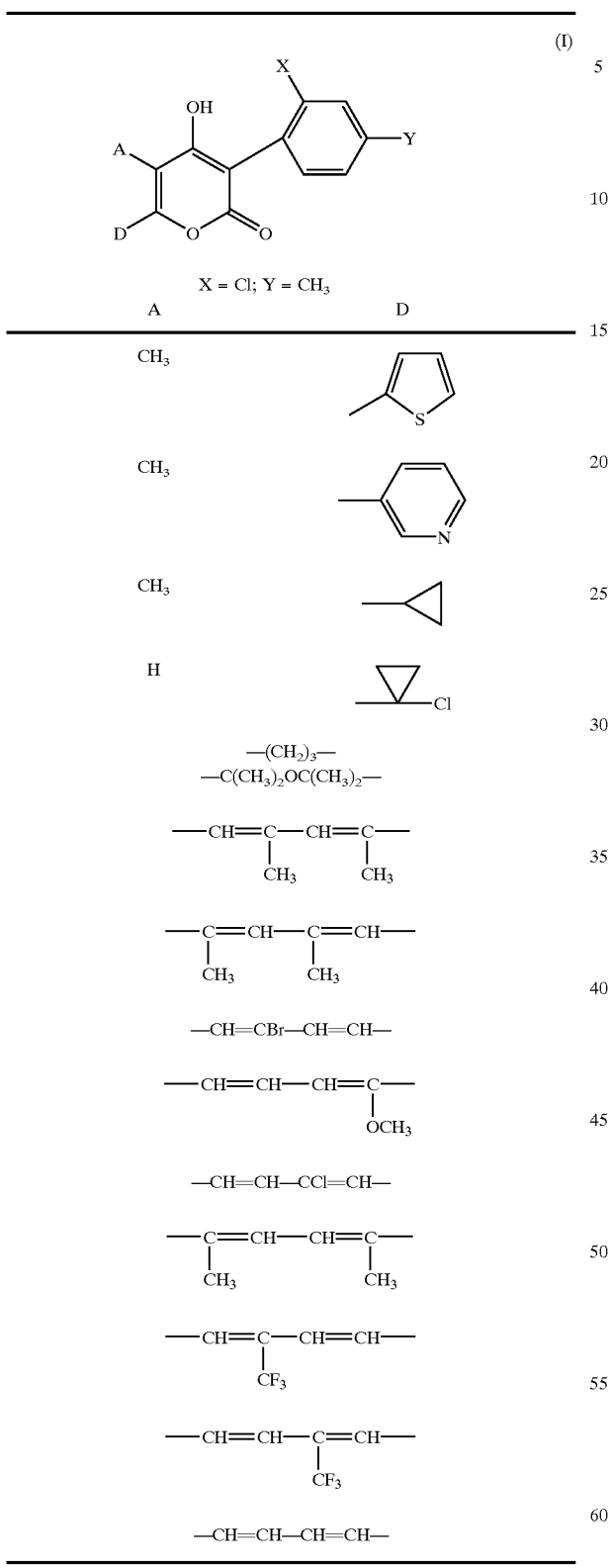

Using chlorocarbonyl 2-(2-methyl-4-chloro-phenyl) ketene and ethyl (pyrid-2-yl) ketone as starting materials, the course of the process according to the invention (variant α) can be illustrated by the following equation:

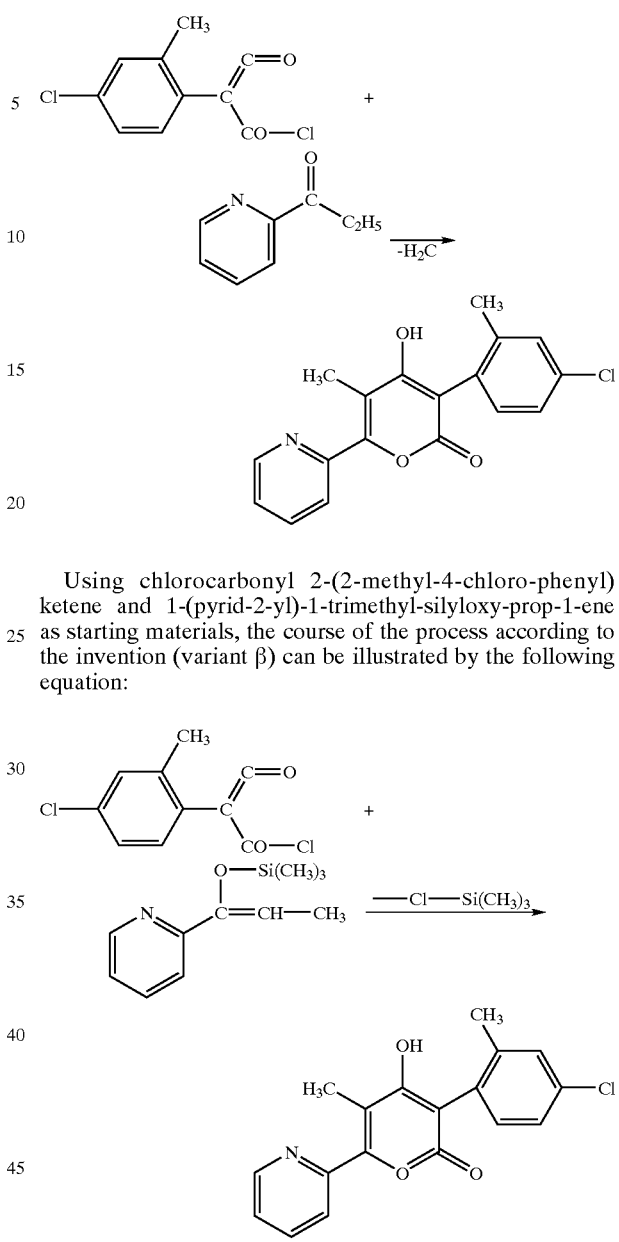

Using chlorocarbonyl 2-(2-methyl-4-chloro-phenyl) ketene and 1-(pyrid-2-yl)-1-trimethyl-silyloxy-prop-1-ene as starting materials, the course of the process according to the invention (variant β) can be illustrated by the following equation:

The formula (II) provides a general definition of the carbonyl compounds required as starting materials for carrying out the process according to the invention, variant α. In this formula, A and D preferably have those meanings which have already been mentioned in connection with the description of the 3-phenyl-pyrones of the formula (I) according to the invention as being preferred for these radicals.

The carbonyl compounds of the formula (II) are known or can be prepared by known processes.

The formula (III) provides a general definition of the silyl ethers required as starting materials for carrying out the process according to the invention, variant β. In this formula, A and D preferably have those meanings which have already been mentioned in connection with the description of the 3-phenyl-pyrones of the formula (I) according to the invention as being preferred for these radicals. Alk preferably represents methyl or ethyl, particularly preferably methyl.

The silyl ethers of the formula (III) are known or can be prepared by known methods.

The formula (IV) provides a general definition of the ketene derivatives required as reaction components for carrying out the process according to the invention. In this formula, X and Y preferably have those meanings which have already been mentioned in connection with the description of the 3-phenyl-pyrones of the formula (I) according to the invention as being preferred for these radicals. Hal also preferably represents chlorine or bromine.

The ketene derivatives of the formula (IV) are known or can be prepared by known processes (cf. Org. Per. Proced. Int. 7, 155–158 (1975) and DE-A 1 945 703). Thus, ketene derivatives of the formula (IV) are obtained by reacting substituted phenylmalonic acids of the formula

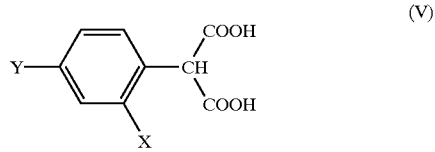

(V)

in which

X and Y are each as defined above with acyl halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-stearyl-formamide or triphenylphosphine, and if appropriate in the presence of bases, such as, for example, pyridine or triethylamine, at a temperature between −20° C. and +200° C., preferably between 0° C. and 150° C.

The substituted phenylmalonic acids of the formula (V) are known or can be prepared by known methods (cf., for example, Organikum, VEB Deutscher Verlag der Wissenschaften, Berlin 1977, p. 517 ff). Thus, substituted phenylmalonic acids of the formula (V) are obtained by reacting substituted phenylmalonic esters of the formula

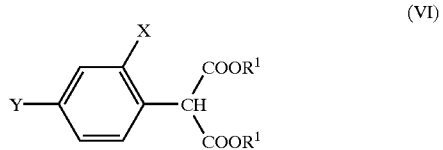

(VI)

in which

X and Y are each as defined above and $R^1$ represents alkyl having 1 to 4 carbon atoms with alkali metal hydroxides, such as sodium hydroxide or potassium hydroxide, in the presence of a diluent, such as water, at temperatures between 0° C. and 30° C.

In the formula (VI), X and Y each preferably have those meanings which have already been mentioned in connection with the description of the 3-phenyl-pyrones of the formula (I) according to the invention as being preferred for these radicals. $R^1$ preferably represents methyl or ethyl.

The substituted phenylmalonic esters of the formula (VI) are known or can be prepared by known methods (cf. Tetrahedron Letters 27, 2763 (1986) and Organikum, VEB Deutscher Verlag der Wissenschaften, Berlin 1977, p. 587 ff.).

Suitable diluents for carrying out the process according to the invention, variants α and β, are all customary organic solvents which are inert towards the reactant participants. Preference is given to using hydrocarbons, such as o-dichlorobenzene, tetraline, toluene and xylene, furthermore ethers, such as dibutyl ether, glycol dimethyl ether and diglycol dimethyl ether, moreover polar solvents, such as dimethyl sulphoxide, sulpholane, dimethylformamide or N-methylpyrrolidone.

Suitable acid acceptors for carrying out the process according to the invention, variants α and β, are all customary acid binders. Preference is given to using tertiary amines, such as triethylamine, pyridine, diazabicyclooctane (DABCO), diazabicycloundecene (DBU), diazabicyclononene (DBN), Hünig base or N,N-dimethyl-aniline.

When carrying out the process according to the invention, variants α and β, the reaction temperatures can be varied within a relatively wide range. Expediently, the reactions are carried out at temperatures between 0° C. and 250° C., preferably between 50° C. and 220° C.

When carrying out the process according to the invention, variants α and β preference is given to operating under atmospheric pressure.

When carrying out the process according to the invention, in general an equimolar amount of ketene derivative of the formula (IV) and, if appropriate, also an equimolar amount of acid acceptor is/are employed per mole of carbonyl compound of the formula (II) and per mole of silyl ether of the formula (III), respectively. However, it is also possible to employ a relatively large excess (up to 5 mol) of one or the other component.

The 3-phenyl-pyrones of the formula (I) to be used according to the invention have very good pesticidal activity and are very well tolerated by crop plants.

The active compounds are suitable for controlling animal pests, preferably arthropods and nematodes, in particular insects and arachnids, which are encountered in agriculture, in forests, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus* From the order of the Chilopoda, for example, *Geophilus carpophagus, Scutigera spec.* From the order of the Symphyla, for example, *Scutigerella immaculata.* From the order of the Thysanura, for example, *Lepisma saccharina.* From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.* From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp. From the order of the Thysanoptera, for example, *Frankliniella occidentalis, Hercinothrips femoralis, Thrips palmi* and *Thrips tabaci.* From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Liriomyza spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention have high insecticidal and acaricidal activity after foliar and soil application.

They can be used particularly successfully for controlling plant-damaging insects, such as, for example, against the larvae of the mustard beetle (*Phaedon cochleariae*), against the larvae of the green rice leaf hopper (*Nephotettix cincticeps*) and against the larvae of the green peach aphid (*Myzus persicae*).

The active compounds according to the invention also have herbicidal activity and can be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The dosages of the active compounds according to the invention required for controlling weeds are between 0.001 and 10 kg/ha, preferably between 0.005 and 5 kg/ha.

The active compounds according to the invention can be employed, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotola, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is by no means restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pastureland, and for the selective control of weeds in annual crops.

Moreover, the 3-phenyl-pyrones of the formula (I) according to the invention also have strong fungicidal activity and can be used for controlling undesirable fungal microorganisms in crop protection and in the protection of materials.

Fungicides can be used in plant protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above are mentioned as examples, but not by way of limitation:

Xanthomonas species, such as, for example, Xanthomonas campestris pv. oryzae;

Pseudomonas species, such as, for example, *Pseudomonas syringae* pv. *lachrymans*;

Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* oder *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, Tilletia caries;
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The fact that the active compounds are well tolerated by plants at the concentrations required for controlling plant diseases permits the treatment of above-ground parts of plants, of propagation stock and seeds, and of the soil.

The active substances to be used according to the invention can be employed particularly successfully for controlling diseases in viticulture, fruit and vegetable growing, such as, for example, against Plasmopara. Moreover, they show good activity against *Pyricularia oryzae* on rice and have a broad fungicidal action both in vitro and in vivo.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound and microencapsulations in polymeric substances.

These formulations are prepared in a known manner, for example by mixing the active compounds with extenders, i.e. liquid solvents and/or solid carriers, optionally with the use of surfactants, i.e. emulsifiers and/or dispersants and/or foam formers.

If the extender used is water, it is also possible to employ for example organic solvents as auxiliary solvents. Suitable liquid solvents are essentially: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water. Suitable solid carriers are:

For example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example, crushed and fractionated natural rocks, such as calcite, marble, pumice, sepiolite, dolomite, or else synthetic granules of inorganic and organic meals, and also granules of organic material, such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolyzates; suitable dispersants are: for example ligninsulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95% by weight of active compound, preferably between 0.5 and 90%, and additionally preferably extenders and/or surfactants.

The active compounds to be used according to the invention can be present in commercial formulations and in use forms prepared from these formulations as a mixture with other active compounds, such as insecticides, attractants, sterilants, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms, etc.

Particularly favourable co-components in mixtures are, for example, the following compounds:
Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoro-methylbenzyl)-benzamide; (E)-2-methoxyimino-N-methyl-2-(2-phenoxyphenyl)-acetamide; 8-hydroxyquinoline sulphate; methyl (E)-2-{2-[6-(2- cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations, such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamates, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin.

Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulphotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides, such as, for example, diflufenican and propanil; arylcarboxylic acids, such as, for example, dichloropicolinic acid, dicamba and picloram; aryloxyalkanoic acids, such as, for example, 2,4-D, 2,4-DB, 2,4-DP, fluroxypyr, MCPA, MCPP and triclopyr; aryloxy-phenoxy-alkanoic esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloracetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulfonylureas, such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiolcarbamates, such as, for example, butylate, cycloate, diallate, EPTC, esprocarb, molinate, prosulfocarb, thiobencarb and triallate; triazines, such as, for example, atrazin, cyanazin, simazin, simetryne, terbutryne and terbutylazin; triazinones, such as, for example, hexazinon, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compounds according to the invention can furthermore be present in their commercially available formulations and in the use forms prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds have an excellent residual action on wood and clay as well as a good stability to alkali on limed substrates.

The active compounds to be used according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, Blatta orientalis, Periplaneta americana, Blattela germanica and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like) so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, of the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:
Beetles, such as

*Hylotrupes bajulus, Chlorophorus pilosis, Anobium punctatum, Xestobium rufovillosum, Ptilinus*

*pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec., Tryptodendron spec., *Apate monachus, Bostrychus capucins, Heterobostrychus brunneus*, Sinoxylon spec., *Dinoderus minutus;*

Dermapterans, such as

Sirex juvencus, Urocerus gigas, Urocerus gigas taignus, Urocerus augur;

Termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;

Bristletails, such as

*Lepisma saccharina.*

Industrial materials are to be understood as meaning, in the present context, non-live materials such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably a-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise further insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinylbutyl carbamate, N-octyl-isothiazolin-3-one and 4,5-dichloro-N-octylisothiazolin-3-one.

The preparation and the use of the active compounds according to the invention is shown in the examples below.

PREPARATION EXAMPLES

Example 1

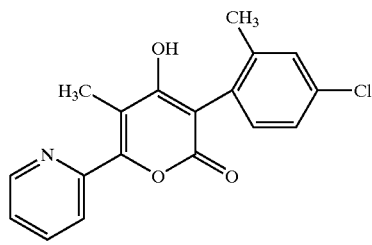

At room temperature, 2.7 g (20 mmol) of ethyl pyrid-2-yl ketone are added with stirring to a mixture of 4.6 g (20 mmol) of chlorocarbonyl 2-(2-methyl-4-chlorophenyl) ketene and 40 ml of anhydrous toluene. The resulting mixture is heated under reflux for 8 hours. After cooling to room temperature, the precipitate which is obtained is filtered off with suction and washed twice with cyclohexane. In this manner, 3.4 g (51% of theory) of 3-(2-methyl-4-chloro-phenyl)-4-hydroxy-5-methyl-6-(pyrid-2-yl)-pyrone are obtained in the form of a solid substance of melting point 133–135° C.

The 3-phenyl-pyrones of the formula (I) listed in Table 4 below are likewise prepared by the abovementioned method.

TABLE 4

(I)

| Ex. No. | A | D | X | Y | Melting point in ° C. |
|---|---|---|---|---|---|
| 2 | H | —C6H4—OCF3 (4-position) | CH3 | F | 254–256 |
| 3 | CH3 | CH3 | CH3 | F | 195–197 |
| 4 | H | —C6H3(2-F)(4-Cl) | CH3 | F | 274–276 |
| 5 | H | —C6H4—O—C6H4—CF3 | CH3 | F | 256–258 |
| 6 | H | —C6H4—CF3 (3-position) | CH3 | Cl | 195–197 |

TABLE 4-continued
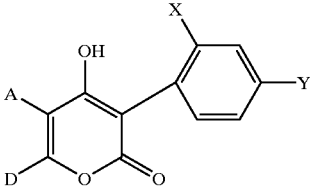
(I)
| Ex. No. | A | D | X | Y | Melting point in °C. |
|---|---|---|---|---|---|
| 7 | H | 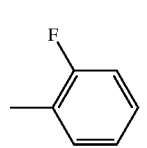 -CF₃ | CH₃ | F | 271–274 |
| 8 | H | 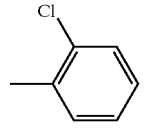 F | CH₃ | F | oil |
| 9 | H | 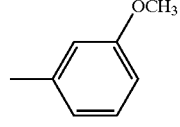 Cl | CH₃ | F | 194–197 |
| 10 | H | 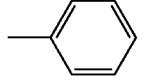 OCH₃ | CH₃ | F | 221–224 |
| 11 | | 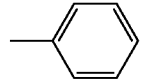 CH₃ | CH₃ | F | 156–158 |
| 12 | CH₃ | 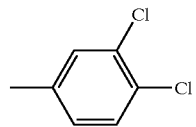 | CH₃ | F | 204–207 |
| 13 | H | 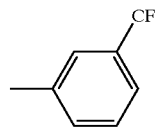 Cl, Cl | CH₃ | F | 280–284 |
| 14 | H | 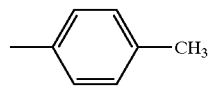 CF₃ | CH₃ | F | 225–227 |
| 15 | H | 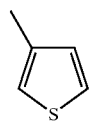 CH₃ | CH₃ | F | 270–273 |
| 16 | H | (3-methylthienyl) | CH₃ | F | oil |
| 17 | | —C(CH₃)₂—O—C(CH₃)₂— | CH₃ | F | 244–246 |
| 18 | —C₂H₅ | CH₃ | CH₃ | F | 131–134 |

TABLE 4-continued (I)

Structure: Pyranone with OH, A, D substituents and phenyl ring bearing X (ortho) and Y (para)

| Ex. No. | A | D | X | Y | Melting point in °C. |
|---|---|---|---|---|---|
| 19 | | —(CH$_2$)$_5$— | CH$_3$ | F | oil |
| 20 | H | 4-NO$_2$-phenyl-CH$_2$— (benzyl with p-NO$_2$) | CH$_3$ | F | 277–279 |
| 21 | | —CH$_2$-(2-methylphenyl) | CH$_3$ | F | >300 |
| 22 | | —CH$_2$—CH(C$_4$H$_9$-t)—(CH$_2$)$_2$— | CH$_3$ | F | 233–335 |
| 23 | | —(CH$_2$)$_4$— | CH$_3$ | F | 195–197 |
| 24 | CH$_3$ | cyclopentyl-CH$_2$— | CH$_3$ | F | 207–209 |
| 25 | CH$_3$ | (6-methylpyridin-3-yl)— | CH$_3$ | F | 130–132 |
| 26 | H | pyridin-3-yl— | CH$_3$ | F | 203–205 |
| 27 | CH$_3$ | 4-Cl-phenyl— | CH$_3$ | F | 211–213 |
| 28 | CH$_3$ | 4-F-phenyl— | CH$_3$ | F | 206–207 |
| 29 | CH$_3$ | —C$_4$H$_9$-t | CH$_3$ | F | 172–174 |
| 30 | CH$_3$ | pyridin-4-yl— | CH$_3$ | F | 253–255 |
| 31 | CH$_3$ | phenyl— | CH$_3$ | Cl | 219–221 |
| 32 | H | (5-Br-thiophen-2-yl)— | CH$_3$ | Cl | oil |

TABLE 4-continued (I)

| Ex. No. | A | D | X | Y | Melting point in °C. |
|---|---|---|---|---|---|
| 33 | H | —C₆H₄—OCF₃ (4-) | CH₃ | Cl | 301–304 |
| 34 | H | —C₆H₄—F (4-) | CH₃ | Cl | 296–297 |
| 35 |  | —(CH₂)₅— | CH₃ | Cl | oil |
| 36 |  | —CH₂—CH(OCH₃)—(CH₂)₂— | CH₃ | Cl | oil |
| 37 |  | —(CH₂)₃— | CH₃ | Cl | 244–247 |
| 38 |  | —CH₂—CH(C₄H₉-t)—(CH₂)₂— | CH₃ | Cl | 224–227 |
| 39 | H | 2,5-dimethylpyridin-yl | CH₃ | Cl | 228–230 |
| 40 | CH₃ | pyridin-3-yl | CH₃ | Cl | 292–293 |
| 41 | H | —CH₂—O—C(O)—(2,5-Cl₂-C₆H₃) | CH₃ | Cl | 90–92 |
| 42 | CH₃ | 2,5-dimethylpyridin-yl | CH₃ | Cl | 229–232 |
| 43 | H | pyridin-3-yl | CH₃ | Cl | 166–168 |
| 44 |  | —C(CH₃)₂—O—C(CH₃)₂— | CH₃ | Cl | 217–219 |
| 45 | CH₃ | CH₃ | CH₃ | Cl | 193–196 |
| 46 | CH₃ | cyclopentyl | CH₃ | Cl | 198–200 |

TABLE 4-continued

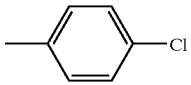

(I)

| Ex. No. | A | D | X | Y | Melting point in °C. |
|---|---|---|---|---|---|
| 47 | CH₃ | —⟨4-Cl-C₆H₄⟩ | CH₃ | Cl | 110–113 |
| 48 | | —(CH₂)₄— | CH₃ | Cl | 94–96 |
| 49 | | —*CH(CH₃)—(CH₂)₃— | CH₃ | Cl | oil |
| 50 | CH₃ | —C₄H₉-t | CH₃ | Cl | 171–173 |
| 51 | CH₃ | —⟨4-pyridyl⟩ | Cl | CH₃ | 350 |
| 52 | H | —⟨4-pyridyl⟩ | Cl | CH₃ | oil |
| 53 | CH₃ | —⟨4-F-C₆H₄⟩ | Cl | CH₃ | 223–225 |
| 54 | | —(CH₂)₄— | Cl | CH₃ | 218–220 |
| 55 | CH₃ | —C₄H₉-t | Cl | CH₃ | oil |
| 56 | CH₃ | —⟨2-pyridyl⟩ | Cl | CH₃ | 112–114 |
| 57 | CH₃ | —cyclopentyl | Cl | CH₃ | 92–95 |
| 58 | H | —⟨3,4-F₂-C₆H₃⟩ | CH₃ | F | oil |
| 59 | | —*CH₂—O—(CH₂)₂— | CH₃ | F | wax |
| 60 | | —*S—(CH₂)₂— | CH₃ | F | oil |
| 61 | | —*CH₂—S—(CH₂)₂— | CH₃ | F | oil |

*) The atom labelled by (*) is in each case attached in the position of the substituent A.

Use Examples

Example A

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, the substances according to the invention disclosed in Examples 1, 42, 46, 56 and 57 exhibit, at an active compound concentration of 0.1% in the preparation of the active compound, an efficacy of more than 90 per cent.

Example B

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the active compound preparation of the desired concentration and are populated with green rice leaf hoppers (Nephotettix cincticeps) while the leaves are still moist.

After the desired period of time, the kill in % is determined. 100% means that all leaf hoppers have been killed; 0% means that none of the leaf hoppers have been killed.

In this test, the substances according to the invention disclosed in Examples 28, 44, 45, 55 and 56 exhibit, at an active compound concentration of 0.1% in the preparation of the active compound, an efficacy of 100 per cent.

Example C

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (Phaedon cochleariae) while the leaves are still moist.

After the desired period of time, the kill in % is determined. 100% means that all beetle larvae have been killed; 0% means that none of the beetle larvae have been killed.

In this test, the substances according to the invention disclosed in Examples 1 and 56 exhibit, at an active compound concentration of 0.1% in the preparation of the active compound, an efficacy of 100 per cent.

Example D

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (Plutella xylostella) while the leaves are still moist.

After the desired period of time, the kill in % is determined. 100% means that all caterpillars have been killed; 0% means that none of the caterpillars have been killed.

In this test, the substances according to the invention disclosed in Examples 24, 45, 46 and 50 exhibit, at an active compound concentration of 0.1% in the preparation of the active compound, an efficacy of 100 per cent.

Example E

*Spodoptera frugiperda* Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into a preparation of active compound of the desired concentration and are populated with caterpillars of the army worm (*Spodoptera frugiperda*) while the leaves are still moist.

After the desired period of time, the kill in % is determined. 100% means that all the caterpillars have been killed; 0% means that none of the caterpillars have been killed.

In this test, the substances according to the invention disclosed in Examples 44 and 56 exhibit, at an active compound concentration of 0.1% in the preparation of active compound, an efficacy of 100 per cent.

Example F

Tetranychus Test (OP-resistant/Dip Treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the kill in % is determined. 100% means that all spider mites have been killed; 0% means that none of the spider mites have been killed.

In this test, the substances according to the invention disclosed in Examples 3, 29, 44, 46 and 50 exhibit, at an active compound concentration of 0.1% in the preparation of active compound, an efficacy of more than 90 per cent.

Example G

Critical Concentration Test/Root-systemic Action

Test insect: *Aphis fabae*

Solvent: 4 parts by weight of dimethylformamide
Emulsifier: 1 part by weight of alkylaryl polyglycol ether To prepare a suitable preparation of active compound, 1 part by weight of active compound is mixed with the stated amount of solvent, the stated amount of emulsifier is added and the concentrate is diluted with water to the desired concentration.

The preparation of active compound is mixed intimately with the soil. The concentration of the active compound in the preparation is virtually immaterial, only the amount by weight of active compound per volume unit of soil, which is stated in ppm (=mg/l), being decisive. The treated soil is filled into 250 ml pots and pre-germinated broad beans are planted in these. Thus, the active compound can be taken up by the plant roots from the soil and then transported into the leaves.

To assess the root-systemic effect, the leaves are populated with the abovementioned test animals after 7 days. After a further 7 days, evaluation is carried out by counting or estimating the dead animals. The root-systemic action of the active compound is derived from the number of animals killed. It is 100% if all test animals have been killed and 0% when the number of test insects that are still alive is the same as for the untreated control.

In this test, the active compound according to the invention disclosed in Example 1 exhibits, at an active compound concentration of 1.25 ppm in the soil, an efficacy of 100 per cent.

Example H
Critical Concentration Test/Root-systemic Action
 Test insect: *Myzus persicae*
 Solvent: 4 parts by weight of dimethylformamide
 Emulsifier: 1 part by weight of alkylaryl polyglycol ether To prepare a suitable preparation of active compound, 1 part by weight of active compound is mixed with the stated amount of solvent, the stated amount of emulsifier is added and the concentrate is diluted with water to the desired concentration.

The preparation of active compound is mixed intimately with the soil. The concentration of the active compound in the preparation is virtually immaterial, only the amount by weight of active compound per volume unit of soil, which is stated in ppm (=mg/ml), being decisive. The treated soil is filled into 250 ml pots and pre-germinated broad beans are planted in these. Thus, the active compound can be taken up by the plant roots from the soil and then transported into the leaves.

To assess the root-systemic effect, the leaves are populated with the abovementioned test animals after 7 days. After a further 7 days, evaluation is carried out by counting or estimating the dead animals. The root-systemic action of the active compound is derived from the number of animals killed. It is 100% if all test animals have been killed and 0% when the number of test insects that are still alive is the same as for the untreated control.

In this test, the active compound according to the invention disclosed in Example 1 exhibits, at an active compound concentration of 1.25 ppm in the soil, an efficacy of 100 per cent.

Example J
Plasmopara Test (Grapevine)/Protective
 Solvent: 47 parts by weight of acetone
 Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of plasmopara viticola and then remain in an incubation cabin at approximately 20° C. and 100% relative atmospheric humidity for 1 day. The plants are subsequently placed in a greenhouse at approximately 21° C. and approximately 90% atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the active compound according to the invention disclosed in Example 57 exhibits, at an application rate of 100 g/ha, an efficacy of more than 80 per cent.

What is claimed is:

1. A 3-phenyl-pyrone of the formula (I)

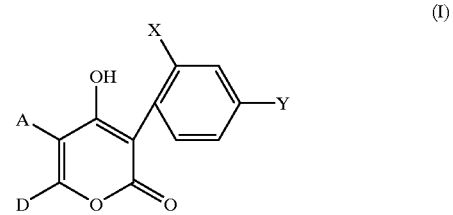

wherein
 X represents alkyl and
 Y represents halogen or
 X represents halogen and
 Y represents alkyl, and
 A represents hydrogen, alkyl or optionally substituted aryl and
 D represents hydrogen, alkyl, optionally substituted cycloalkyl, optionally substituted aryl or optionally substituted heterocyclyl, or
 D represents a radical of the formula

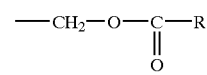

wherein
 R represents optionally substituted phenyl, or
 A and D together with the carbon atoms to which they are attached represent an optionally substituted carbocycle or represent an optionally substituted heterocycle,
except for the compounds of the formulae

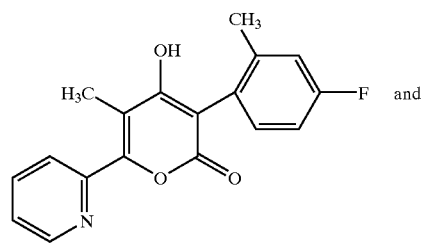 and

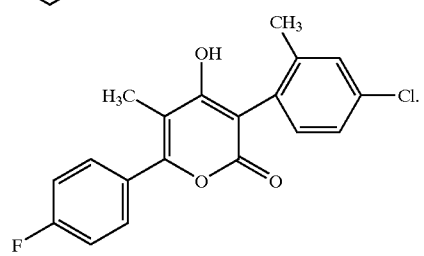

2. The compound of claim 1 wherein
 X represents alkyl having 1 to 6 carbon atoms and
 Y represents fluorine, chlorine or bromine or X represents fluorine, chlorine or bromine and Y represents alkyl having 1 to 6 carbon atoms, and A represents hydrogen, alkyl having 1 to 12 carbon atoms or represents phenyl which may be unsubstituted or mono- to trisubstituted by substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano and nitro, D represents hydrogen, alkyl having 1 to 12 carbon atoms, represents cycloalkyl having 3 to 8 carbon atoms which is unsubstituted or substituted by halogen, alkyl having 1 to 4 carbon atoms, alkoxy having 1 to 4 carbon atoms and/or halogenoalkyl having 1 to 4 carbon atoms, or represents phenyl which may be unsubstituted or mono- to trisubstituted by substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano, nitro, phenyl and phenoxy, wherein the two last mentioned radicals may be unsubstituted or mono- or disubstituted by halogen, $C_1$–$C_4$-alkyl, $C_1$–$C_4$-alkoxy, $C_1$–$C_4$-halogenoalkyl and/or $C_1$–$C_4$-halogenoalkoxy, or represents 5- or 6-membered heteroaryl having 1 or 2 heteroatoms selected from the group consisting of oxygen, sulphur and nitrogen, which may be unsubstituted or mono- or disubstituted by halogen, $C_1$–$C_6$-alkyl, $C_1$–$C_6$-halogenoalkyl, $C_1$–$C_6$-alkoxy, $C_1$–$C_6$-halogenoalkoxy, cyano and/or nitro, or represents a radical of the formula

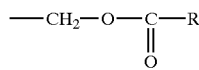

wherein

R represents phenyl which may be unsubstituted or mono- to trisubstituted by substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano and nitro, A and D together represent a $C_3$–$C_6$-alkanediyl, $C_3$–$C_6$-alkenediyl or $C_4$–$C_6$-alkanedienediyl group wherein optionally one methylene group is replaced by oxygen or sulphur, and which may be optionally substituted by halogen, $C_1$–$C_6$-alkyl, $C_1$–$C_6$-halogenoalkyl, $C_1$–$C_6$-alkoxy, $C_1$–$C_6$-halogenoalkoxy, or by a further $C_3$–$C_6$-alkanediyl-, $C_3$–$C_6$-alkenediyl- or $C_4$–$C_6$-alkanedienediyl group which forms a fused-on ring wherein optionally one methylene group is replaced by oxygen or sulphur and which may be unsubstituted or substituted by $C_1$–$C_6$-alkyl, except for the compounds of the formulae

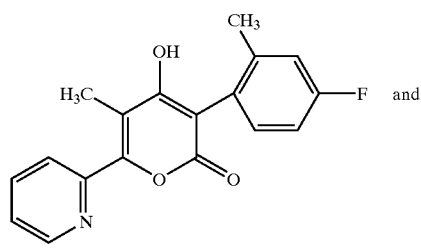 and

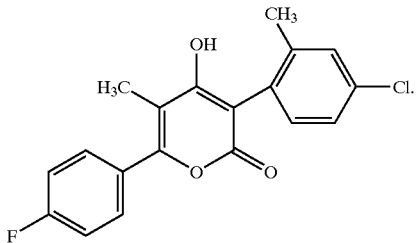

3. The compound of claim 1 wherein

X represents alkyl having 1 to 4 carbon atoms and

Y represents fluorine, chlorine or bromine or

X represents chlorine or bromine and

Y represents alkyl having 1 to 4 carbon atoms, and

A represents hydrogen, alkyl having 1 to 8 carbon atoms or represents phenyl which may be unsubstituted or mono- to trisubstituted by substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and nitro, D represents hydrogen, alkyl having 1 to 10 carbon atoms, or represents cycloalkyl having 3 to 7 carbon atoms which is unsubstituted or mono- to trisubstituted by substituents selected from the group consisting of fluorine, chlorine, $C_1$–$C_3$-alkyl, $C_1$–$C_2$-alkoxy, $C_1$–$C_2$-halogenoalkyl, or represents phenyl which may be unsubstituted or mono- to trisubstituted by substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano, nitro, phenyl and phenoxy, wherein the two last mentioned radicals may be unsubstituted or mono- or disubstituted by fluorine, chlorine, bromine, methyl, ethyl, methoxy, trifluoromethyl, trifluoromethoxy and/or difluoromethoxy, or represents furanyl, pyridyl, imidazolyl, triazolyl, pyrazolyl, pyrimidinyl, thiazolyl or thienyl, which may be unsubstituted or mono- or disubstituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and/or nitro, or D represents a radical of the formula

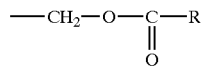

wherein

R represents phenyl which may be unsubstituted or mono- to trisubstituted by substituents selected from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano and nitro, A and D together represent a $C_3$–$C_5$-alkanediyl or $C_3$–$C_5$-alkenediyl group wherein optionally one carbon atom is replaced by oxygen or sulphur and which are unsubstituted or substituted by fluorine, chlorine, bromine, $C_1$–$C_4$-alkyl, $C_1$–$C_4$-alkoxy, $C_1$–$C_4$-halogenoalkyl and/or $C_1$–$C_6$-halogenoalkoxy, or by a further $C_4$-alkanedienediyl group which forms a fused-on ring and which may be unsubstituted or substituted by $C_1$–$C_4$-alkyl, except for the compounds of the formulae

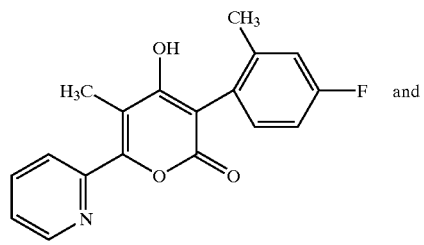

and

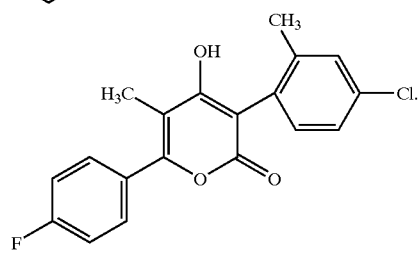

4. The compound of claim 1 wherein
X represents methyl or ethyl and
Y represents fluorine or chlorine or
X represents chlorine or bromine and
Y represents methyl or ethyl, and
A represents hydrogen, alkyl having 1 to 6 carbon atoms or represents phenyl which may be unsubstituted or mono- or disubstituted by substituents selected from the group consisting of fluorine, chlorine, methyl, ethyl, n-propyl, isopropyl, trifluoromethyl, methoxy, ethoxy, trifluoromethoxy, cyano and nitro,
D represents hydrogen, alkyl having 1 to 8 carbon atoms, or represents cycloalkyl having 3 to 7 carbon atoms which is unsubstituted or mono- or disubstituted by substituents selected from the group consisting of fluorine, chlorine, methyl, ethyl, methoxy, ethoxy and/or trifluoromethyl,
or represents phenyl which may be unsubstituted or mono- or disubstituted by substituents selected from the group consisting of fluorine, chlorine, bromine, methyl, ethyl, n-propyl, isopropyl, n-butyl, sec-butyl, iso-butyl, tert-butyl, trifluoromethyl, methoxy, ethoxy, trifluoromethoxy, cyano, nitro, phenyl and phenoxy, wherein the two last mentioned radicals may be unsubstituted or mono- or disubstituted by fluorine, chlorine, methyl, methoxy, trifluoromethyl and trifluoromethoxy,
or represents furanyl, pyridyl or thienyl, which may be unsubstituted or mono- or disubstituted by fluorine, chlorine, bromine, methyl, ethyl, n-propyl, isopropyl, trifluoromethyl, trifluoromethoxy, cyano and/or nitro, or
D represents a radical of the formula

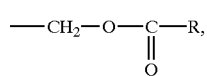

wherein
R represents phenyl which may be unsubstituted or mono- or disubstituted by substituents selected from the group consisting of fluorine, chlorine, methyl, ethyl, trifluoromethyl, methoxy, trifluoromethoxy, cyano and nitro, A and D together represent a $C_3$–$C_5$-alkanediyl or $C_3$–$C_5$-alkenediyl group wherein optionally one methylene group is replaced by oxygen or sulphur and which is unsubstituted or mono- to tetra-substituted by substituents selected from the group consisting of fluorine, chlorine, bromine, methyl, ethyl, n-propyl, isopropyl, n-butyl, iso-butyl, sec-butyl, tert-butyl, methoxy, trifluoro-methyl and trifluoromethoxy, or by a further butadienediyl group which forms a fused-on ring and which may be unsubstituted or mono- or disubstituted by methyl,
except for the compounds of the formulae

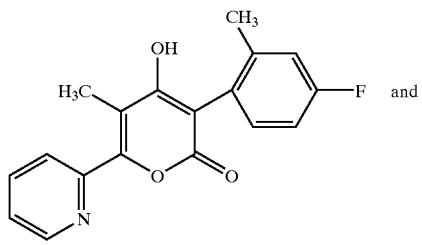

and

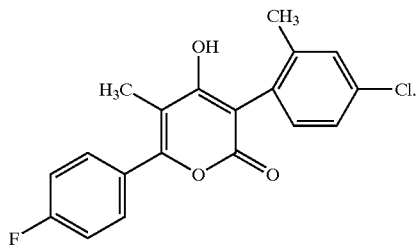

5. A process for preparing a 3-phenyl-pyrone of claim 1, comprising reacting a compound selected from
a carbonyl compound of the formula (II)

(II)

wherein
A and D are as defined in claim 1 and a silyl ether of the formula (III)

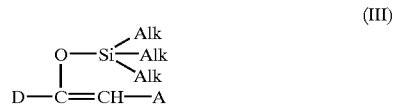

(III)

wherein
A and D are as defined in claim 1 and
Alk represents alkyl having 1 to 4 carbon atoms with a ketene of the formula (IV)

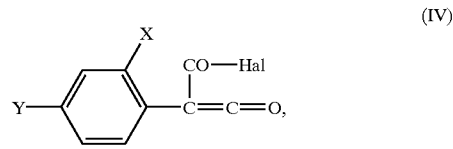

(IV)

wherein
X and Y are as defined in claim 1 and
Hal represents chlorine or bromine, and collecting the reaction product.

6. A pesticidal, fungicidal and herbicidal composition comprising at least one 3-phenyl-pyrone of claim 1 and at least one of extenders and surfactants.

7. A method for controlling at least one animal pest comprising applying at least one 3-phenyl-pyrone of claim 1 to the pest and/or its habitat.

8. A method for controlling fungi, comprising applying at least one 3-phenyl-pyrone of claim 1 to the fungi and/or its habitat.

9. A method for controlling at least one weed comprising applying at least one 3-phenyl-pyrone of claim 1 to the weed and/or its habitat.

10. A process for preparing a pesticidal, fungicidal and herbicidal composition comprising mixing at least one 3-phenyl-pyrone of claim 1 with at least one of extenders and surfactants, and collecting the product.

* * * * *